United States Patent [19]

Bristol et al.

[11] 4,452,788

[45] Jun. 5, 1984

[54] SUBSTITUTED 8-PHENYLXANTHINES

[75] Inventors: James A. Bristol, Ann Arbor; Edward W. Badger, Dexter, both of Mich.

[73] Assignee: Warner-Lambert Company, Morris Plains, N.J.

[21] Appl. No.: 370,649

[22] Filed: Apr. 21, 1982

[51] Int. Cl.$^3$ .................... C07D 239/96; A61K 31/52
[52] U.S. Cl. .................................. 424/253; 544/267; 544/266
[58] Field of Search ................ 544/267, 266; 424/253

[56] References Cited

FOREIGN PATENT DOCUMENTS 982079  2/1965  United Kingdom .

OTHER PUBLICATIONS

Proc. Natl. Acad. Sci. U.S.A. 77 5547 (1980).

*Primary Examiner*—Nicholas S. Rizzo
*Attorney, Agent, or Firm*—Jerry F. Janssen

[57] ABSTRACT

Substituted 8-phenylxanthines and their use as bronchodilators is described. Methods for their preparation and use as well as pharmaceutical compositions containing them are also described.

14 Claims, No Drawings

SUBSTITUTED 8-PHENYLXANTHINES

BACKGROUND OF THE INVENTION

The use of certain substituted 8-phenylxanthine compounds as adenosine receptor antagonist agents is described in Proc. Natl. Acad. Sci. USA, 77, 5547 (1980). The reference discloses the use of 8-(4-sulfophenyl)-theophylline, also named as 4-(1,3-dimethyl-2,3,6,7-tetrahydro-2,6-dioxo-1H-purin-8-yl)benzenesulfonic acid.

SUMMARY OF THE INVENTION

The invention sought to be patented in its generic chemical compound aspect is a compound having the structural formula

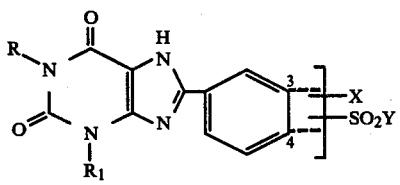

wherein R and $R_1$ may be the same or different and are hydrogen, alkyl of from one to six carbon atoms, hydroxyalkyl of from two to six carbon atoms, $(CH_2)_{2-4}$-$N(R_3)_2$ wherein $R_3$ is alkyl of from one to six carbon atoms, $Ph(CH_2)_{1-3}$ or $CF_3(CH_2)_{1-4}$; the dashed lines mean that the two substituents may only be in the three or four positions; X is hydrogen, halogen, hydroxy, alkyl of from one to six carbon atoms, alkoxy of from one to six carbon atoms, acylamino of from two to seven carbon atoms or $NR_4R_5$ wherein $R_4$ and $R_5$ are hydrogen or alkyl of from one to six carbon atoms; Y is OA wherein A is hydrogen or a pharmaceutically acceptable cation derived from a metal or an amine, or $NR_6R_7$ wherein $R_6$ is hydrogen, hydroxyalkyl of from two to six carbon atoms or alkyl of from one to six carbon atoms, $R_7$ is hydrogen, alkyl of from one to six carbon atoms, or $(CH_2)_{2-6}$—$NR_8R_9$ wherein $R_8$ and $R_9$ are hydrogen, alkyl of from one to six carbon atoms or when taken together form

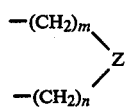

wherein m and n may be the same or different and are 1, 2, or 3 provided that the sum of m and n is an integer of from three to six and Z is a direct bond, O, S—$(O)_k$ wherein k is 0, 1, or 2, or N—$R_{10}$ wherein $R_{10}$ is hydrogen or alkyl of from one to six carbon atoms; or $R_6$ and $R_7$ when taken together form

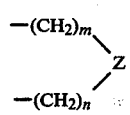

wherein m, n, and Z are defined above; and the pharmaceutically acceptable salts thereof; with the proviso that the compound 8-(4-sulfophenyl)theophylline is excluded.

The invention sought to be patented in a first subgeneric aspect of its chemical compound aspect is a compound having the structural formula

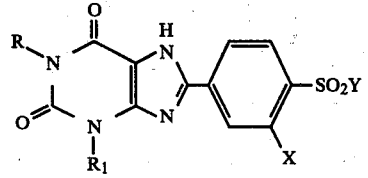

and the pharmaceutically acceptable salts thereof wherein R, $R_1$, X, and Y are defined above; with the proviso that the compound 8-(4-sulfophenyl)theophylline is excluded.

The invention sought to be patented in a second subgeneric aspect of its chemical compound aspect is a compound having the structural formula

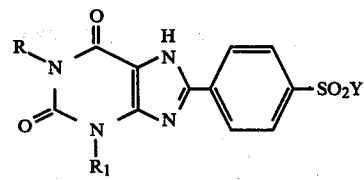

and the pharmaceutically acceptable salts thereof, wherein R, $R_1$, and Y are defined above; with the proviso that the compound 8-(4-sulfophenyl)theophylline is excluded.

The invention sought to be patented as species of its organic chemical compound aspect are the compounds having the names:
4-(1,3-Diethyl-2,3,6,7-tetrahydro-2,6-dioxo-1H-purin-8-yl)benzenesulfonic acid;
3-(1,3-Diethyl-2,3,6,7-tetrahydro-2,6-dioxo-1H-purin-8-yl)benzenesulfonic acid;
3-(1,3-Diethyl-2,3,6,7-tetrahydro-2,6-dioxo-1H-purin-8-yl)-N-[2-(dimethylamino)ethyl]benzenesulfonamide;
(S)-4-(1,3-Diethyl-2,3,6,7-tetrahydro-2,6-dioxo-1H-purin-8-yl)-N-(2-hydroxypropyl)benzenesulfonamide;
4-(1,3-Diethyl-2,3,6,7-tetrahydro-2,6-dioxo-1H-purin-8-yl)-N-[2-(dimethylamino)ethyl]benzenesulfonamide;
4-(1,3-Diethyl-2,3,6,7-tetrahydro-2,6-dioxo-1H-purin-8-yl)-N-[3-(dimethylamino)propyl]benzenesulfonamide;
1-[[4-(1,3-Diethyl-2,3,6,7-tetrahydro-2,6-dioxo-1H-purin-8-yl)phenyl]sulfonyl]-4-methylpiperazine;
4-[[4-(1,3-Diethyl-2,3,6,7-tetrahydro-2,6-dioxo-1H-purin-8-yl)phenyl]sulfonyl]morpholine;
4-(1,3-Diethyl-2,3,6,7-tetrahydro-2,6-dioxo-1H-purin-8-yl)benzenesulfonamide;
4-[[4-(1,3-Diethyl-2,3,6,7-tetrahydro-2,6-dioxo-1H-purin-8-yl)phenyl]sulfonyl]thiomorpholine;
4-(1,3-Dipropyl-2,3,6,7-tetrahydro-2,6-dioxo-1H-purin-8-yl)benzenesulfonic acid; and
N-[2-(Dimethylamino)ethyl]-4-(2,3,6,7-tetrahydro-2,6-dioxo-1,3-dipropyl-1H-purin-8-yl)benzenesulfonamide;
and their pharmaceutically acceptable salts.

The invention sought to be patented in its chemical process aspect is a process for preparing a compound having the structural formula

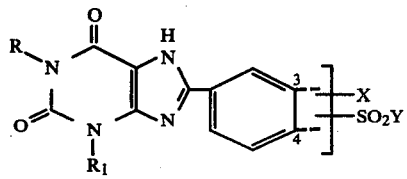

which comprises reacting a compound having the structural formula

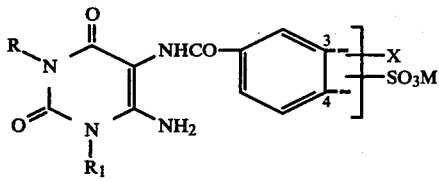

with a base to produce a compound having the structural formula

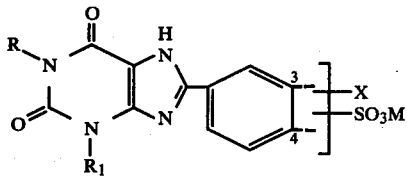

and converting the so obtained sulfonic acid salt to a corresponding sulfonic acid or a corresponding sulfonamide having the structural formula

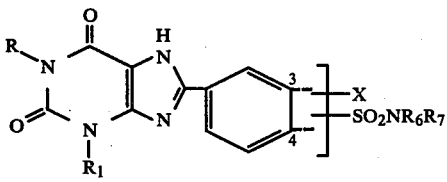

wherein R, $R_1$, $R_6$, $R_7$, X, and Y are defined above and M is a convenient metal or amine.

The invention sought to be patented in its pharmaceutical composition aspect is a composition useful for treating bronchoconstriction in a mammal consisting essentially of a compound having the structural formula I or mixtures thereof, in combination with a pharmaceutically acceptable carrier.

The invention sought to be patented in its pharmaceutically method aspect is a method for treating bronchoconstriction in a mammal in need of such treatment; which comprises administering an effective amount of the above defined pharmaceutical composition to said mammal.

DESCRIPTION OF THE PREFERRED EMBODIMENTS

The compounds of the invention having structural formula Ia

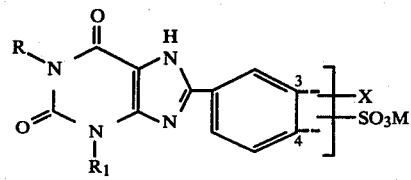

may be conveniently prepared by the reaction of a properly substituted 5,6-diaminouracil, II

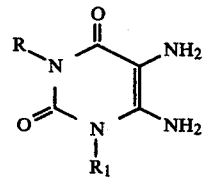

with a substituted benzoic acid having the structural formula III

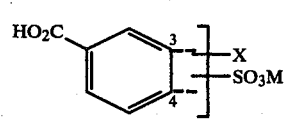

wherein R, $R_1$, the dashed lines, M and X have the definitions given above. This reaction may be carried out for example, by mixing approximate equimolar quantities of II and III in a nonreactive solvent in the presence of an amide forming reagent such as 1-ethyl-3-(3-dimethylaminopropyl)carbodiimide (EDAC), cyclohexylcarbodiimide (DCC), and the like. When EDAC is utilized, a convenient solvent is water at pH=6. Other methods for amide formation such as mixed anhydride methods using for example ethyl chloroformate are useful and will be familiar to those skilled in the art.

The product of this reaction has the structural formula IV

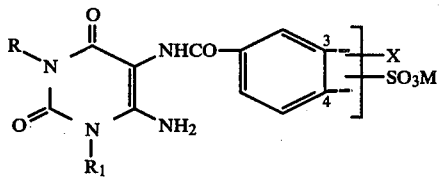

and is next treated with aqueous base such as sodium hydroxide preferably at elevated temperature to produce the salts Ia. The salts Ia, are themselves compounds of the invention and are readily converted to the corresponding free sulfonic acids by treatment with an acid. For example, dilute hydrochloric acid may be utilized. The sulfonic acids so obtained may be readily converted to pharmaceutically acceptable metal or amine salts by treatment with the desired base using standard procedures.

The free sulfonic acids prepared as above may be converted to a corresponding sulfonyl halide such as the chloride or bromide and treated with a desired amine to produce the compounds of formula I wherein Y is $NR_6R_7$, wherein $R_6$ and $R_7$ are as defined above. The conversion of the sulfonic acids to a corresponding sulfonic acid halide may be accomplished by the use of thionyl chloride, thionyl bromide, phosphorous oxychloride and the like.

In the preferred procedure, the sulfonic acid is converted to the corresponding sulfonyl chloride by treatment with thionyl chloride in N,N-dimethylformamide, (DMF). This conversion is preferably carried out by dissolving the sulfonic acid in DMF, cooling the solution externally to about 0° C. and adding the thionyl chloride undiluted and in one portion with rapid stirring. The cooling bath is removed and the mixture is stirred and allowed to reach room temperature over a period of about one hour. The sulfonic acid chloride so produced is preferably not isolated and may be permitted to react with a large excess (ca. 5–10 molar equivalents) of an amine, $HNR_6R_7$. Alternatively, the reaction mixture may be concentrated at reduced pressure and the resulting mixture may be dissolved in pyridine and treated with between 1 and 2 molar equivalents of the amine $HNR_6R_7$ thereby producing the products I wherein Y is $NR_6R_7$.

The starting materials III, are either commercially available or they may be prepared by standard methods or by obvious variations thereof. For example, 3-sulfobenzoic acid is described in Beilstein 11, 384 and 4-sulfobenzoic acid is described in Beilstein 11, 389.

The starting 5,6-diaminouracils having structural formula II may be prepared from the corresponding 6-aminouracils, for example, by the procedure described in J. Am. Chem. Soc., 76, 2798 (1954) which procedure is incorporated herein by reference. The requisite 6-aminouracils may be prepared as described in J. Org. Chem., 16, 1879 (1951) or by obvious variations of the methods described therein.

The compounds of the invention having structural formula I display adenosine receptor antagonism when assayed by the procedure described in Proc. Natl. Acad. Sci. USA, 77, 5547 (1980). The relevant teachings of this manuscript are incorporated herein by reference.

When assayed by the above referenced procedure the following results were obtained for representative compounds of the invention.

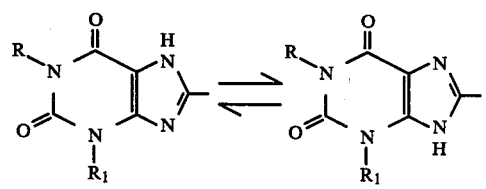

| R | $R_1$ | X | Y' | $IC_{50}$ nM |
|---|---|---|---|---|
| $C_2H_5$ | $C_2H_5$ | H | 3-$SO_3K$ | 37,000 |
| $C_2H_5$ | $C_2H_5$ | H | 4-$SO_3K$ | 4,900 |
| $C_2H_5$ | $C_2H_5$ | H | 3-$SO_2NH(CH_2)_2N(CH_3)_2$ | 550 |
| n-$C_3H_7$ | n-$C_3H_7$ | H | 4-$SO_3K$ | 100 |
| n-$C_3H_7$ | n-$C_3H_7$ | H | 4-$SO_2NH(CH_2)_2N(CH_3)_2$ | 10 |
| $C_2H_5$ | $C_2H_5$ | H | 4-$SO_2NH_2$ | 50 |
| $C_2H_5$ | $C_2H_5$ | H | 4-$SO_2N(CH_2CH_2)_2O$ | 300 |
| $C_2H_5$ | $C_2H_5$ | H | 4-$SO_2NH(CH_2)_3N(CH_3)_2$ | 70 |
| $C_2H_5$ | $C_2H_5$ | H | 4-$SO_2N(CH_2CH_2)_2NCH_3$ | 150 |
| $CH_3$ | $CH_3$ | H | 4-$SO_3H$ | 20,000* |
| theophylline | | | | 15,000* |

*Results reported in Proc. Natl. Acad. Sci. USA, 77, 5547(1980).

Theophylline which possesses a variety of pharmacological effects (Goodman and Gillman, The Pharmacological Basis of Therapeutics, sixth edition, Macmillan Publishing Co., Inc., 1980, Chapter 25) is a clinically useful bronchodilator and is used for the treatment of bronchoconstriction and asthma, ibid. It is believed that the bronchodilator effects and other effects of theophylline may be due to this compound's inhibition of the effects of endogenous adenosine [Agents and Actions, 10, 145(1980); Trends in Pharmacological Sciences, 129, January 1980]. Because of the superior adenosine receptor antagonism activity demonstrated by the compounds of the invention, they are expected to possess similar diuretic, cardiotonic, central nervous system stimulant, and bronchodilator effects to theophylline but at lower doses.

Those skilled in the art will recognize that the compounds of the invention having structural formula I may exist in tautomeric forms.

Both such tautomeric forms of the compounds as well as mixtures thereof are included by the invention. For reasons of convenience only one such tautomeric structural formula has been utilized herein.

The compounds of the invention form pharmaceutically acceptable salts with both organic and inorganic acids and bases. Examples of suitable acids for salt formation are hydrochloric, sulfuric, phosphoric, acetic, citric, oxalic, malonic, salicylic, malic, fumaric, succinic, ascorbic, maleic, methansulfonic, and the like. The salts are prepared by contacting the free base form with an equivalent amount of the desired acid in the conventional manner. The free base forms may be regenerated by treating the salt form with a base. For example, dilute aqueous base solutions may be utilized. Dilute aqueous sodium hydroxide, potassium carbonate, ammonia and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

Examples of suitable bases for salt formation are sodium hydroxide, sodium carbonate, sodium bicarbonate, potassium hydroxide, calcium hydroxide, ammonia, organic amines, and the like. The salts are prepared by contacting the free acid form with an equivalent amount of the desired base in the conventional manner. The free acid forms may be regenerated by treating the salt form with an acid. For example, dilute aqueous acid solutions may be utilized. Dilute aqueous hydrochloric acid, sulfuric acid or acetic acid are suitable for this purpose. The free acid forms differ from their respective salt forms somewhat in certain physical properties such as solubility in polar solvents, but the salts are otherwise equivalent to their respective free acid forms for purposes of the invention.

The compounds of the invention can exist in unsolvated as well as solvated forms, including hydrated forms. In general, the solvated forms, with pharmaceutically acceptable solvents such as water, ethanol, and the like are equivalent to the unsolvated forms for purposes of the invention.

The alkyl groups and alkoxy groups contemplated by the invention comprise both straight and branched carbon chains of from one to about six carbon atoms. Representative of such groups are methyl, ethyl, isopropyl, pentyl, 3-methylpentyl, methoxy, ethoxy, i-propoxy, and the like.

The term acylamino is intended to mean a group of the structural formula—NHCOAlk wherein Alk is a straight or branched carbon chain of from one to about six carbon atoms as exemplified above.

Some of the compounds of the invention may comprise an asymmetric carbon atom which may be present for example in a substituent such as an alkyl group. The pure R isomer, pure S isomer, as well as mixtures thereof are contemplated by the invention.

The term halogen is intended to include fluorine, chlorine, and bromine.

The term Ph means the phenyl group, $C_6H_5$.

The compounds of the invention can be prepared and administered in a wide variety of oral and parenteral dosage forms. Inhalation dosage forms as well as suppositories are also contemplated.

It will be obvious to those skilled in the art that the following dosage forms may comprise as the active component, either a compound of formula I, or a corresponding pharmaceutically acceptable salt of a compound of formula I, or a mixture of such compounds and/or salts.

For preparing pharmaceutical compositions from the compounds described by this invention, inert, pharmaceutically acceptable carriers can be either solid or liquid. Solid form preparations include powders, tablets, dispersable granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium sterate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be packaged preparation, the package containing discrete quantities of preparation, for example, packeted tablets, capsules and powders in vials or ampoules. The unit dosage form can also be a capsule, cachet, or tablet itself or it can be the appropriate number of any of these packaged forms.

The quantity of active compound in a unit dose of preparation may be varied or adjusted from 1 mg to 100 according to the particular application and the potency of the active ingredient.

In therapeutic use as bronchodilating agents, the compounds utilized in the pharmaceutical method of this invention are administered at a daily dose range of about 0.25 mg to about 4 mg per kilogram. A daily dose of about 0.6 mg to about 1.6 mg per kilogram is preferred. The dosages, however, may be varied depending upon the requirements of the patient, the severity of the condition being treated, and the compound being employed. Determination of the proper dosge for a particular situation is within the skill of the art. Generally, treatment is initiated with smaller doses which are less than the optimum dose of the compound. Thereafter, the dose is increased by small increments until the optimum effect under the circumstances is reached. For convenience, the total daily dose may be divided and administered in portions during the day if desired.

The following nonlimiting examples illustrate the inventors' preferred methods for preparing the compounds of the invention.

EXAMPLE 1

4-(1,3-Diethyl-2,3,6,7-tetrahydro-2,6-dioxo-1H-purin-8-yl)benzenesulfonic acid

A mixture of 5,6-diamino-1,3-diethyl-2,4(1H,3H)-pyrimidinedione (41.2 g, 0.208 moles), 4-sulfobenzoic acid monopotassium salt (50.0 g, 0.208 moles), and water (250 ml) is prepared, and the pH adjusted to 6.0. Ethyl-3-(3-dimethylaminopropyl)carbodiimide (39.9 g, 0.208 moles) is added in one portion, and the pH of the resulting solution maintained at 5.5±0.5 with the dropwise addition of 4 N hydrochloric acid. When the pH of the solution ceases to rise, the mixture is concentrated on a rotary evaporator, and the residue taken up in 400 ml 10% potassium hydroxide and stirred for 18 hours. At the end of this time, the solution is boiled under reflux for one hour, cooled, filtered, and made acidic with the portionwise addition of 12 N hydrochloric acid. The resulting suspension is cooled and filtered; the solids are triturated with ethanol, filtered, and dried to yield 51.2 grams of 4-(1,3-diethyl-2,3,6,7-tetrahydro-2,6-dioxo-1H-purin-8-yl)-benzenesulfonic acid; mp greater than 360° C.

EXAMPLE 2

3-(1,3-Diethyl-2,3,6,7-tetrahydro-2,6-dioxo-1H-purin-yl)benzenesulfonic acid potassium salt A mixture of 5,6-diamino-1,3-diethyl-2,4-(1H,3H)-pyrimidinedione (10.0 g, 0.0504 moles) and 3-sulfobenzoic acid monosodium salt (13.1 g, 0.0504 moles) and water (275 ml) is prepared, and the pH adjusted to 5.0 with 2 N sodium hydroxide. To this solution is added ethyl-3-(3-dimethylaminopropyl)carbodiimide (10.45 g, 0.05045 moles), and the pH of the resulting solution maintained at pH 5.0±0.5 by the dropwise addition of 4 N hydrochloric acid. When the pH ceases to rise, the reaction mixture is distilled on a rotary evaporator, and the residue taken up in 250 ml of 10% potassium hydroxide. This solution is boiled under reflux for 30 minutes, cooled, and treated with 100 ml of 50% potassium hydroxide. A heavy precipitate results which is filtered and washed with 10% potassium hydroxide then dried at 48° in a vacuum oven to yield 5.61 grams of 3-(1,3-diethyl-2,3,6,7-tetrahydro-2,6-dioxo-1H-purin-8-yl)benzenesulfonic acid potassium salt, mp greater than 360° C.

EXAMPLE 3

3-(1,3-Diethyl-2,3,6,7-tetrahydro-2,6,-dioxo-1H-purin-8-yl)-N-[2-(dimethylamino)ethyl]benzenesulfonamide A mixture of 3-(1,3-diethyl-2,3,6,7-tetrahydro-2,6-dioxo-1H-purin-8-yl)benzenesulfonic acid monopotassium salt (4.6 g, 0.01 moles) and DMF (250 ml) is prepared and cooled to 0° C. To this solution is added thionyl chloride (7.14 g, 0.06 mole) and the mixture allowed to come to ambient temperature with vigorous stirring. To this slurry is added unsym dimethylethylenediamine (17.6 g, 0.2 moles). The resulting solution is concentrated on a rotary evaporator, the residue taken up in water, filtered, recrystallized twice from ethanol and dried at 48° to yield 0.78 grams of 3-(1,3-diethyl-2,3,6,7-tetrahydro-2,6-dioxo-1H-purin-8-yl)-N-[2-(dimethylamino)ethyl]benzenesulfonamide, mp, 250°-251° C.

Analysis for: ($C_{19}H_{26}N_6O_4S \cdot \frac{1}{2}H_2O$): C, 51.45, H, 6.14, N, 18.94, S, 7.23, KF, 2.03. Found: C, 51.19, H, 5.88, N, 18.45, S, 7.62, KF, 1.14.

EXAMPLE 4

(S)-4-(1,3-Diethyl-2,3,6,7-tetrahydro-2,6-dioxo-1H-purin-8-yl)-N-(2-hydroxypropyl)benzenesulfonamide A mixture of 4-(1,3-diethyl-2,3,6,7-tetrahydro-2,6-dioxo-1H-purin-8-yl)benzenesulfonic acid (4.84 g, 0.0133 moles), N,N-dimethylformamide (150 ml), and thionyl chloride (3.16 g, 0.266 moles) is prepared and stirred until a thick slurry results. To this slurry is added S(+)-1-amino-2-propanol (10.0 g, 0.133 moles) in one portion. The resulting mixture is stirred until a clear solution results, and distilled on a rotary evaporator. The residue is taken up in water, filtered, and recrystallized from ethanol to yield 3.6 grams of (S)-4-(1,3-diethyl-2,3,6,7-tetrahydro-2,6-dioxo-1H-purin-8-yl)-N-(2-hydroxypropyl)benzenesulfonamide mp, 283°-285° C.

Analysis for ($C_{18}H_{23}N_5O_5S \cdot \frac{1}{2}H_2O$) C, 50.57, H, 5.58, N, 16.38, S, 7.50, KF, 1.40 Found: C, 50.22, H, 5.21, N, 16.32, S, 7.92, KF, 1.77. $\alpha_D^{23}$ −4.5° (C 1.065, 0.1 N NaOH).

EXAMPLE 5

4-(1,3-Diethyl-2,3,6,7-tetrahydro-2,6-dioxo-1H-purin-8-yl)-N-[2-(dimethylamino)ethyl]benzenesulfonamide A mixture of 4-(1,3-diethyl-2,3,6,7-tetrahydro-2,6-dioxo-1H-purin-8-yl)benzenesulfonic acid, (7.0 g, 0.019 moles) and N,N-dimethylformamide (125 ml) is cooled to 0°, and treated with thionyl chloride (4.6 g, 0.038 moles). When the addition is complete, the reaction mixture is permitted to warm to ambient temperature, and stirred vigorously for one hour. The resulting slurry is cooled to 0°, and treated with unsym dimethylethylenediamine (8.8 g, 0.10 mole) and allowed to warm to ambient temperature. The reaction mixture is concentrated on a rotary evaporator, the residue is taken up in cool water and filtered. The solid thus obtained is recrystallized from ethanol and dried at 78° in a drying pistol to give 5.87 grams of 4-(1,3-diethyl-2,3,6,7-tetrahydro-2,6-dioxo-1H-purin-8-yl)-N-[2-(dimethylamino)ethyl]benzenesulfonamide, mp 264°-265° C.(d).

Analysis for ($C_{19}H_{26}N_6O_4S$): C, 52.52, H, 6.03, N, 19.34, S, 7.38. Found: C, 52.35, H, 6.04, N. 19.24, S, 6.81.

EXAMPLE 6

4-(1,3-Diethyl-2,3,6,7-tetrahydro-2,6-dioxo-1H-purin-8-yl)-N-[3-(dimethylaminopropyl]benzenesulfonamide monohydrochloride A mixture of 4-(1,3-diethyl-2,3,6,7-tetrahydro-2,6,-dioxo-1H-purin-8-yl)benzenesulfonic acid, (5.0 g, 0.014 moles) and N,N-dimethylformamide (150 ml) is cooled to 0° and treated with thionyl chloride (3.3 g, 0.027 moles). When the addition is complete, the reaction mixture is permitted to warm to ambient temperature and stirred vigorously until a thick slurry is formed. To this slurry is added 3-(dimethylamino)propylamine (14 g, 0.137 moles) in one portion, the mixture is stirred until a clear solution is obtained, and concentrated on a rotary evaporator. The residue is taken up in water, filtered, recrystallized from ethanol, and dried at 78° to yield 1.53 grams of 4-(1,3-diethyl-2,3,6,7-tetrahydro-2,6-dioxo-1H-purin-8-yl)-N-[3-(dimethylamino)propyl]benzenesulfonamide monohydrochloride, mp 291°-292° C.(d).

Analysis for ($C_{20}H_{28}N_6O_4S \cdot HCl \cdot \frac{1}{2}H_2O$): C, 48.63, H, 6.12, N, 17.01, Cl, 7.18, S, 6.49, KF, 1.80. Found: C, 48.86, H, 6.05, N, 17.14, Cl, 6.60, S, 7.28, KF, 2.01.

EXAMPLE 7

1-[[4-(1,3-Diethyl-2,3,6,7-tetrahydro-2,6,-dioxo-1H-purin-8-yl)phenyl]sulfonyl]-4-methyl-piperazine A mixture of 4-(1,3-diethyl-2,3,6,7-tetrahydro-2,6-dioxo-1H-purin-8-yl)benzenesulfonic acid (5.0 g, 0.014 moles) and N,N-dimethylformamide (150 ml) is cooled to 0° and treated with thionyl chloride (3.3 g, 0.027 moles). When the addition is complete, the reaction mixture is permitted to warm to ambient temperature and stirred vigorously until a thick slurry results. To this slurry is added N-methylpiperazine (13.7 g, 0.137 moles) in one portion, the mixture is stirred until a clear solution is obtained, and concentrated on a rotary evaporator. The residue is taken up in water, filtered, recrystallized from ethanol, and dried at 48° to yield 5.12 grams of 1-[[4-(1,3-diethyl-2,3,6,7-tetrahydro-2,6-dioxo-1H-purin-8-yl)phenyl]sulfonyl]4-methylpiperazine, mp 305°-307° C.

Analysis for ($C_{20}H_{26}N_4O_4S$): C, 53.80, H, 5.87, N, 18.82, S, 7.18. Found: C, 53.60, H, 5.83, N, 18.90, S, 7.47.

EXAMPLE 8

4-[[4-(1,3-Diethyl-2,3,6,7-tetrahydro-2,6-dioxo-1H-purin-8-yl)phenyl]sulfonyl]morpholine A mixture of 4-(1,3-diethyl-2,3,6,7-tetrahydro-2,6-dioxo-1H-purin-8-yl)benzenesulfonic acid (5.0 g, 0,014 moles) and N,N-dimethylformamide (150 ml) is cooled to 0° and treated with thionyl chloride (3.3 g, 0.027 moles). When the addition is complete, the reaction mixture is permitted to warm to ambient temperature and stirred vigorously until a thick slurry results. To this slurry is added morpholine (20 g, 0.23 moles) in one portion. The resulting slurry is stirred one hour and poured into two liters of water. The resulting suspension is filtered, triturated with ethanol, and dried at 68° to yield 3.29 grams of 4-[[4-(1,3-diethyl-2,3,6,7-tetrahydro-2,6-dioxo-1H-purin-8-yl)phenyl]sulfonyl]morpholine, mp 354°–355° C.(d).

Analysis for ($C_{19}H_{23}N_5O_5S$): C, 52.65, H, 5.35, N, 16.16, S, 7.40. Found: C, 52.41, H, 5.27, N, 16.17, S, 7.71.

EXAMPLE 9

4-(1,3-Diethyl-2,3,6,7-tetrahydro-2,6-dioxo-1H-purin-8-yl)benzenesulfonamide

A mixture of 4-(1,3-diethyl-2,3,6,7-tetrahydro-2,6-dioxo-1H-purin-8-yl)benzenesulfonic acid (5.0 g, 0.014 moles) and N,N-dimethylformamide (150 ml) is cooled to 0° and treated with thionyl chloride (3.3 g, 0.027 moles). When the addition is complete, the reaction mixture is permitted to warm to ambient temperature and stirred vigorously until a thick slurry results. To this slurry is added N,N-dimethylformamide saturated with ammonia (100 ml). The resulting mixture is then saturated with gaseous ammonia and concentrated on a rotary evaporator. The residue is taken up in water, filtered, triturated with ethanol and dried at 68° C. to yield 2.9 grams of 4-(1,3-diethyl-2,3,6,7-tetrahydro-2,6-dioxo-1H-purin-8-yl)benzenesulfonamide, mp 350°–353° C.(d).

Analysis for ($C_{15}H_{17}N_5O_4S$): C, 49.58, H, 4.72, N, 19.27, S, 8.82. Found: C, 49.63, H, 4.80, N, 19.03, S, 8.81.

EXAMPLE 10

4-[[4-(1,3-Diethyl-2,3,6,7-tetrahydro-2,6-dioxo-1H-purin-8-yl)phenyl]sulfonyl]thiomorpholine A mixture of 4-(1,3-diethyl-2,3,6,7-tetrahydro-2,6-dioxo-1H-purin-8-yl)benzenesulfonic acid (10.0 g, 0.0274 moles) and N,N-dimethylformamide (300 ml) is cooled to 0° C. and treated with thionyl chloride (6.5 g, 0.055 moles). When the addition is complete, the reaction mixture is permitted to warm to ambient temperature and stirred vigorously until a thick slurry results. To this slurry is added thiomorpholine (14.2 g, 0.137 moles) in one portion. The resulting mixture is stirred one hour, poured into three liters of water, and filtered. The solids thus obtained are tritruated with ethanol and dried at 48° in a vacuum oven to yield 11.9 grams of 4-[[4-(1,3-diethyl-2,3,6,7-tetrahydro-2,6-dioxo-1H-purin-8-yl)phenyl]sulfonyl]thiomorpholine, mp 340°–350° C.(d).

Analysis for ($C_{19}H_{23}N_5O_4S_2$): C, 50.76, H, 5.16, N, 15.58, S, 14.26. Found: C, 50.87, H, 5.25, N, 15.61, S, 14.55.

EXAMPLE 11

4-(1,3-dipropyl-2,3,6,7-tetrahydro-2,6-dioxo-1H-purin-8-yl)benzenesulfonic acid potassium salt A mixture of 5,6-diamino-1,3-dipropyl-2,4-(1H,3H)pyrimidinedione (16.0 g, 0.07 moles), 4-sulfobenzoic acid monopotassium salt (17.0 g, 0.0707 moles) and water (250 ml) is prepared, and the pH adjusted to 5.0 by the addition of 10% potassium hydroxide. To this solution is added ethyl-3-(3-dimethylaminopropyl)carbodiimide (13.6 g, 0.0707 moles) in one portion, and the pH maintained at 5.0±0.5 by the dropwise addition of 4 N hydrochloric acid. When the pH stabilizes, the reaction mixture is treated with sodium hydroxide (100 ml, 50%), boiled under reflux for ten minutes, treated with activated carbon, and filtered warm. The resulting solution is chilled in ice, treated with hydrochloric acid (12 N, 1350 ml), and filtered. The solids are dried, recrystallized from methanol, and dried at 78° to yield 5.12 grams of 4-(1,3-dipropyl-2,3,6,7-tetrahydro-2,6-dioxo-1H-purin-8-yl)benzenesulfonic acid potassium salt, mp greater than 360°.

EXAMPLE 12

N-[2-(Dimethylamino)ethyl]-4-(2,3,6,7-tetrahydro-2,6-dioxo-1,3-dipropyl-1H-purin-8-yl)benzenesulfonamide A mixture of 4-(1,3-dipropyl-2,3,6,7-tetrahydro-2,6-dioxo-1H-purin-8-yl)benzenesulfonic acid (3.93 g, 0.01 moles) and N,N-dimethylformamide (100 ml) is prepared, cooled to 0° C., treated with thionyl chloride (2.4 g, 0.02 moles), and permitted to warm to ambient temperature with vigorous stirring. The resulting slurry is cooled to 0° C., treated with a solution of unsym dimethylethylenediamine (8.8 g, 0.10 mole) in N,N-dimethylformamide (11 ml) added in one portion, and allowed to warm to ambient temperature. The resulting solution is concentrated on a rotary evaporator. The residue is suspended in water, filtered, recrystallized from ethanol, and dried at 78° to yield 0.60 grams of N-[2-(dimethylamino)ethyl]-4-(2,3,6,7-tetrahydro-2,6-dioxo-1,3-dipropyl-1H-purin-8-yl)benzenesulfonamide, mp, 270°–272° C.(d).

Analysis for ($C_{21}H_{30}N_6O_4S$): C, 54.53, H, 6.54, N, 18.17, S, 6.93. Found: C, 54.49, H, 6.58, N, 18.93, S, 7.17.

PREPARATIVE EXAMPLE 1

5,6-Diamino-1,3-diethyl-2,4-(1H,3H)pyrimidinedione

A suspension of 5-amino-1,3-diethyl-2,4-(1H,3H)pyrimidinedione (133.0 g, 0.726 moles) and sodium nitrite (55.2 g, 0.80 moles) in water (2000 ml) is prepared and treated with hydrochloric acid (12 N, 73.3 ml, 0.88 moles) after the manner of Blicke [J. Am. Chem. Soc., 76, 2798, (1954)] to yield 6-amino-1,3-diethyl-5-nitroso-2,4-(1H,3H)pyrimidinedione, which is filtered from the reaction mixture, and dried. The product is suspended in water (1500 ml) and treated with sodium dithionite, which is added portionwise in quantity to effect complete decolorization of the nitroso compound. The resulting suspension is filtered, the solids treated with 10% potassium hydroxide and filtered. These solids are collected and dried at 48° in a drying oven to yield 125 grams 5,6-diamino-1,3-diethyl-2,4-(1H,3H)pyrimidinedione.

PREPARATIVE EXAMPLE 2

5,6-diamino-1,3-Dipropyl-2,4-(1H,3H)pyrimidinedione

A mixture of 5-amino-1,3-dipropyl-2,4-(1H,3H)pyrimidinedione (52.8 g, 0.25 moles), sodium nitrite (20.7 g, 0.30 moles) and water (1000 ml) is prepared and treated with hydrochloric acid (12 N, 30 ml, 0.35 moles) after the method of Blicke (J. Am. Chem. Soc., 76, 2798 (1954)]. 6-Amino-1,3-dipropyl-5-nitroso-2,4-(1H,3H)pyrimidinedione is collected as described and is used as obtained in the next step. The nitroso compound is suspended in water (500 ml) and treated with sodium dithionite, added portionwise in a quantity sufficient to effect decolorization of the purple nitroso compound. The resulting slurry is treated with sodium hydroxide (100 ml 50%), chilled, and filtered. The solids thus obtained are dried at 78° in a vacuum oven to yield 34.4 g of 5,6-diamino-1,3-dipropyl-2,4-(1H,3H)pyrimidinedione.

We claim:

1. A compound having the structural formula

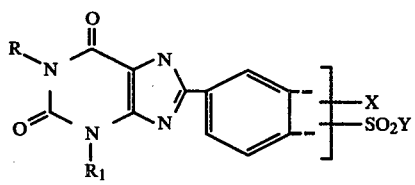

wherein R and $R_1$ may be the same or different and are hydrogen, alkyl of from one to six carbon atoms, hydroxyalkyl of from two to six carbon atoms, $(CH_2)_{2-4}N(R_3)_2$ wherein $R_3$ is alkyl of from one to six carbon atoms, $Ph(CH_2)_{1-3}$ or $CF_3(CH_2)_{1-4}$; the dashed lines mean that the two substituents may only be in the three or four positions; X is hydrogen, halogen, hydroxy, alkyl of from one to six carbon atoms, or $NR_4R_5$ wherein $R_4$ and $R_5$ are hydrogen or alkyl of from one to six carbon atoms, Y is $NR_6R_7$ wherein $R_6$ is hydrogen, hydroxyalkyl of from two to six carbon atoms or alkyl of from one to six carbon atoms, $R_7$ is hydrogen, alkyl of from one to six carbon atoms, or $(CH_2)_{2-6}-NR_8R_9$ wherein $R_8$ and $R_9$ are hydrogen, alkyl of from one to six carbon atoms or when taken together form

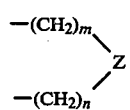

wherein m and n may be the same or different and are 1, 2, or 3 provided that the sum of m and n is an integer of from three to six and Z is a direct bond, O, S—(O)$_k$ wherein k is 0, 1, or 2 or N-$R_{10}$ wherein $R_{10}$ is hydrogen or alkyl of from one to six carbon atoms; or $R_6$ and $R_7$ when taken together form

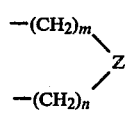

wherein m, n, and z are defined above; and the pharmaceutically acceptable salts thereof.

2. The compounds defined in claim 1 having the structural formula

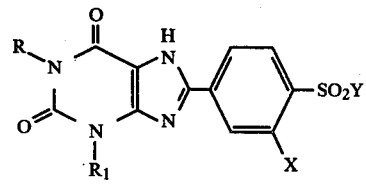

and the pharmaceutically acceptable salts thereof.

3. The compounds defined in claim 1 having the structural formula

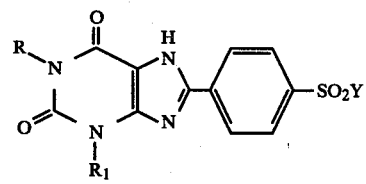

and the pharmaceutically acceptable salts thereof.

4. The compound defined in claim 1 having the name 3-(1,3-diethyl-2,3,6,7-tetrahydro-2,6-dioxo-1H-purin-8-yl)-N-[2-(dimethylamino)ethyl]benzenesulfonamide; and the pharmaceutically acceptable salts thereof.

5. The compound defined in claim 1 having the name (S)-4-(1,3-diethyl-2,3,6,7-tetrahydro-2,6-dioxo-1H-purin-8-yl)-N-(2-hydroxypropyl)benzenesulfonamide; and the pharmaceutically acceptable salts thereof.

6. The compound defined in claim 1 having the name 4-(1,3-diethyl-2,3,6,7-tetrahydro-2,6-dioxo-1H-purin-8-yl)-N-[2-(dimethyamino)ethyl]benzenesulfonamide; and the pharmaceutically acceptable salts thereof.

7. The compound defined in claim 1 having the name 4-(1,3-diethyl-2,3,6,7-tetrahydro-2,6-dioxo-1H-purin-8-yl)-N-[3-(dimethylamino)propyl]benzenesulfonamide; and the pharmaceutically acceptable salts thereof.

8. The compound defined in claim 1 having the name 1-[[4-(1,3-diethyl-2,3,6,7-tetrahydro-2,6-dioxo-1H-purin-8-yl)phenyl]sulfonyl]-4-methylpiperazine; and the pharmaceutically acceptable salts thereof.

9. The compound defined in claim 1 having the name 4-[[4-(1,3-diethyl-2,3,6,7-tetrahydro-2,6-dioxo-1H-purin-8-yl)phenyl]sulfonyl]morpholine; and the pharmaceutically acceptable salts thereof.

10. The compound defined in claim 1 having the name 4-(1,3-diethyl-2,3,6,7-tetrahydro-2,6-dioxo-1H-purin-8-yl)benzenesulfonamide; and the pharmaceutically acceptable salts thereof.

11. The compound defined in claim 1 having the name 4-[[4-(1,3-diethyl-2,3,6,7-tetrahydro-2,6-dioxo-1H-purin-8-yl)phenyl]sulfonyl]thiomorpholine; and the pharmaceutically acceptable salts thereof.

12. The compound defined in claim 1 having the name N-[2-(dimethylamino)ethyl]-4-(2,3,6,7-tetrahydro-2,6-dioxo-1,3-dipropyl-1H-purin-8-yl)benzenesulfonamide; and the pharmaceutically acceptable salts thereof.

13. A pharmaceutical composition useful for treating bronchoconstriction comprising a compound as defined in claim 1 and the pharmaceutically acceptable salts thereof in combination with a pharmaceutically acceptable carrier.

14. A method for treating bronchoconstriction in a mammal which comprises administering a sufficient amount of the pharmaceutical composition defined in claim 13 to a mammal in need thereof.

* * * * *